US000001551H

United States Statutory Invention Registration [19]

[11] Reg. Number: H1551

Tsuchiya

[45] Published: Jun. 4, 1996

[54] TOPICAL COMPOSITION AND METHOD FOR REDUCING HAIR LOSS FROM HUMAN SCALP

[76] Inventor: Wakoh Tsuchiya, 32, Shimogamo-shimogawara-cho, Sakyo-ku, Kyoto, Japan

[21] Appl. No.: 132,487

[22] Filed: Oct. 6, 1993

Related U.S. Application Data

[63] Continuation of Ser. No. 899,593, Jun. 18, 1992, abandoned, which is a continuation of Ser. No. 729,861, Jul. 10, 1991, abandoned, which is a continuation of Ser. No. 559,416, Jul. 25, 1990, abandoned, which is a continuation of Ser. No. 426,525, Oct. 24, 1989, abandoned, which is a continuation of Ser. No. 91,769, Aug. 27, 1987, abandoned, which is a continuation of Ser. No. 659,870, Oct. 12, 1984, abandoned, which is a continuation of Ser. No. 475,924, Mar. 16, 1983, abandoned.

[30] Foreign Application Priority Data

| | | | |
|---|---|---|---|
| Mar. 20, 1982 | [JP] | Japan | 57-45103 |
| Sep. 24, 1982 | [JP] | Japan | 57-166193 |
| Sep. 24, 1982 | [JP] | Japan | 57-166194 |

[51] Int. Cl.[6] ..... A61K 31/56

[52] U.S. Cl. ..... 514/178

[58] Field of Search ..... 514/178

[56] References Cited

U.S. PATENT DOCUMENTS 3,856,829 12/1974 Hiraga et al. ..... 260/397.4

4,272,508 6/1981 Tamm ..... 424/243

OTHER PUBLICATIONS

Federal Register, 21CFR Part 310 Tues Jan. 15, 1985 pp. 2190–2198.

Chemical Abstracts (1973) vol. 79 Par. 73,914s.

*Primary Examiner*—Donald P. Walsh
*Assistant Examiner*—Anthony R. Chi

[57] ABSTRACT

The present invention concerns a novel hair grower without exerting undesirable side-effects, which is topically applicable. The hair grower contains a maximum of about 2% of oxendolone in combination with a topically applicable vehicle or carrier, if desired, with further conventional additives.

4 Claims, 3 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

TOPICAL COMPOSITION AND METHOD FOR REDUCING HAIR LOSS FROM HUMAN SCALP

This application is a continuation of now abandoned application Ser. No. 07/899,593, filed Jun. 18, 1992, which application is a continuation of now abandoned application Ser. No. 07/729,861, filed Jul. 10, 1991, which application is a continuation of now abandoned application Ser. No. 07/559,416, filed Jul. 25, 1990, which application is a continuation of now abandoned application Ser. No. 07/426,525, filed Oct. 24, 1989, which application is a continuation of now abandoned application Ser. No. 07/091,769, filed Aug. 27, 1987, which application is a continuation of now abandoned application Ser. No. 06/659,870, filed Oct. 12, 1984, which application is a continuation of now abandoned application Ser. No. 06/475,924, filed Mar. 16, 1983.

This invention relates to a hair grower which does not exhibit undesirable side-effects such as systemic hormonal activity but has an excellent hair growing effect by topical application.

Testosterone (male hormone) produced in the testicles and adrenal gland is carried in the blood stream and reaches the sebaceous gland where it is converted to 5α-dihydrotestosterone (5α-DHT), a more potent male hormone, by the reductase present in the cells of the sebaceous gland.

Physiological symptoms such as male pattern baldness (MPB) and seborrhea are said to develop as a result of excessive androgen stimulation due to an excessive local accumulation of testosterone.

Recently, the active form of male hormone in such organs as the hair root and sebaceous gland has been identified to be 5α-DHT which is produced by reduction of testosterone in these organs by an enzyme called testosterone-5α-reductase (briefly, reductase). The mechanism involved in the pathogenesis of MPB may be postulated as follows. While 5α-DHT, which is produced in the sebaceous tissue, combines with a receptor in the sebaceous cells and acts on the nucleus to promote the growth of the cells, 5α-DHT itself comes out of the sebaceous gland cells and is carried in the blood stream and acts on the nearby cells, i.e. hair matrix to inhibit division of the hair matrix cells and prevent growth of the hair.

It is therefore believed that such conditions as male pattern baldness or alopecia areata can be reduced or prevented by inhibiting the activity of the reductase and the binding of 5α-DHT with the receptor protein in the hair matrix. From this standpoint, several substances have been discovered up to date. However, none of these substances have proved to be a satisfactory hair grower, because even if they have a high rate of inhibition of the reductase activity, they usually have undesirable side-effects or they show a low rate of inhibition of the binding of 5α-DHT with the receptor protein.

In view of the above circumstances, the present inventor has made extensive investigations in order to search for a substance which has no undesirable side-effect such as systemic hormonal activity, is safe, and shows an effect of inhibiting both the activity of the reductase and the binding of 5α-DHT with the receptor protein by topical use. In other words, these investigations have led to the discovery that the above object can be achieved by employing oxendolone. The present invention was accomplished based on this discovery.

Oxendolone, which is used in this invention, is chemically known as 16β-ethyl-17β-hydroxy-4-estren-3-one which is available as a white or pale yellowish white, odorless powder. It is available on the market as a drug for benign prostatic hypertrophy and while it is administered intramuscularly as an aqueous suspension containing 200 mg per 2 ml (Prostetin: Trade name of Takeda Chemical Industries, Ltd., U.S. Pat. No. 3,856,829), it has never been applied as a topical agent. The present hair grower contains a maximum of about 2% of oxendolone in combination with a topically applicable vehicle or carrier, and if desired with further usual additives. Preferably, the grower may contain more than about 0.001% of oxendolone and, more desirably, 0.05 to 0.2% thereof in the total preparation. Oxendolone is practically insoluble in water but soluble, for example, in ethanol, and, therefore, aqueous ethanol containing more than 30%, preferably 50% of ethanol may be employed as a suitable vehicle. Oxendolone also may be dissolved totally or partially in vegetable oils such as sesame oil, cottonseed oil, castor oil, olive oil, corn oil, peanut oil, etc., carbohydrates such as squalane, squalene, liquid paraffin, vaseline, etc., alcohols such as palmityl alcohol, hexadecyl alcohol, stearyl alcohol, oleyl alcohol, propylene glycol, polyethylene glycol, polypropylene glycol, etc., fatty acids such as myristic acid, palmitic acid, stearic acid, oleic acid, etc., or silicone oils, lanoline, etc. The hair grower of the present invention may optionally contain any of those additives normally used in hair grower or hair tonics, for example germicides such as hinokitiol, surface active agents, refreshing agents such as menthol, perfumes, antioxidants, ultraviolet absorbers, dyes, moisturizers such as urea, salicylic acid, polyglyceride glycerol, etc.

The present hair grower may be used in the form of a liquid as well as emulsions, ointments, etc., prepared by a conventional method, and can be applied several times (1 to 6 times) a day in an amount of about 0.5–10 ml, preferably 1–5 ml. However, the amount and application interval may vary with the conditions of the subject and may be used in a range of 0.1 mg to 100 mg per day, preferably 1 to 5 mg per day as oxendolone. In other words, the regimen of this invention prescribes rubbing 0.05 ml/cm$^2$ of the present drug well into the bare or downy patches of the scalp several times (1 to 6 times) a day. The grower is preferably used after a shampooing. It causes no particular side effect, but its use is preferably avoided in the presence of an open wound.

Toxicity Test of the Present Hair Grower:

No local acute toxicity was observed when 0.05 ml/cm$^2$ of the 0.2% ethanol solution of oxendolone was applied to the affected area several times a day. However, frequent applications may result in dryness of the hair and scalp, when ethanol, etc. is used. No other systemic or local side effect was observed in the application schedule.

The systemic acute toxicity of oxendolone is as follows:

| | | Acute Toxicity ($LD_{50}$: mg/kg) | |
|---|---|---|---|
| | | Intramuscular | Intraperitoneal |
| Mouse | Male | Above 10,000 | 2,930 |
| | Female | Above 10,000 | 2,980 |
| Rat | Male | Above 10,000 | 6,530 |
| | Female | Above 10,000 | 5,880 |

It is well known that androgen is related to premature baldness. To cure or arrest this condition, it is important to inhibit 5α-reductase activity and 5α-DHT activity in the sebaceous gland. It was found that "Oxendolone" of the present hair grower possesses not only the above two activities but also the one to inhibit uptake of testosterone into the cells. It was also found that these activities of oxendolone, coupled with the defatting actions of "ethanol", would synergistically produce a decrease of head sebum and promote the mitosis of basal cells of hair, rendering soft hair hard.

The effect of the oxendolone used in this invention to inhibit the activity of the reductase and the binding of 5α-DHT with the receptor protein will be described below by citing a comparative example.

Inhibitory Effect on the Reductase Activity

Based on the method of Takayasu et al. (The Nishinihon Journal of Dermatology, 43, 1215–1217, 1981), the amount of testosterone reduced to 5α-DHT was measured by using the sebaceous gland at the back of a hamster. The concentrations of the samples used in the experiment were $10^{-4}$ and $10^{-5}$ molar concentrations, respectively. The rate of inhibition was calculated from the following equation using the resulting data. The results are shown in Table 1.

Rate of inhibition (%)=(C–t/C) ×100

C: the amount of 5α-DHT formed in a control t: the amount of 5α-DHT formed when the sample was added

TABLE 1

| Drug | Rate of inhibition Molar concentration $10^{-4}$ | $10^{-5}$ |
|---|---|---|
| Oxendolone | 43 ± 18% | 28 ± 28% |
| 4-andronsten-3-one-17-carboxylic acid | 54 ± 32% | 31 ± 19% |

Inhibitory Effect of Oxendolone on Binding of 5α-DHT with the Receptor Protein Based on the method of Takayasu et al. (Arch. Dermatol. Res., 264, 50–51, 1979), the amount of 5α-DHT bound with the receptor protein was measured. The concentration of the sample used in the experiment was $10^{-6}$ molar concentration. The rate of inhibition was calculated from the following equation using the resulting data. The results are shown in Table 2.

Rate of inhibition (%)=(C–t/C)×100

C: the amount of 5α-DHT bound with the receptor protein in a control t: the amount of 5α-DHT bound with the receptor protein when the sample was added

TABLE 2

| Chemicals | Rate of inhibition |
|---|---|
| Oxendolone | 53% |
| 4-andronsten-3-one-17β-carboxylic acid | 0% |

It is seen from Tables 1 and 2 that while oxendolone has an equivalent inhibitory effect on the reductase activity to the known 4-androsten-3-one-17β-carboxylic acid, its inhibitory effect on the binding of 5α-DHT with the receptor protein is greater, and that oxendolone can be said to be a substance which achieves the object of this invention. Hence, it is expected that the hair grower of this invention containing oxendolone has a great hair growing effect.

The following examples illustrate the present invention in greater detail. The present invention is not limited to these examples. The amounts incorporated are % by weight.

Method of Measuring the Hair-Growing Effect

It was evaluated by changes in the number of hairs lost during hair washing before and after using the hair grower. Ten subjects were used for each of Examples 1 to 3 and Comparative Example 1. The period of measurement was 4 months. In the first two months, the hair grower was not applied, and in the latter two months, the hair grower was applied. The hair was shampooed on every third day. The hairs which were lost were collected once a week, and their number was counted. The number of the lost hairs recovered eight times in total during the two months in which period no hair grower was applied, and the number of the lost hairs collected eight times in total during the two months in which period the hair grower was applied, were counted. The number of the lost hairs for each time was indicated by employing the symbol + and –. The effect was evaluated as shown below from the difference between the average values of the two periods.

++: The number of the lost hairs decreased by more than 70, and a marked effect was observed.

+: The number of the lost hairs decreased by more than 40, and a considerable effect was observed.

±: The number of the lost hairs decreased by more than 10, and it could be said that a little effect was obtained.

–: The number of the lost hairs decreased by less than 10, and it could not be said that there was an effect.

EXAMPLES 1 to 3 and COMPARATIVE EXAMPLE 1

| Chemicals | Example 1 | Example 2 | Example 3 | Comparative Example 1 |
|---|---|---|---|---|
| Oxendolone | 0.001 | 0.2 | 2.0 | — |
| 95% Ethanol | 60.0 | 60.0 | 60.0 | 60.0 |
| Deionized water | 37.999 | 37.8 | 36.0 | 37.9 |
| Hardened castor oil/40 mole E0 adduct | 2.0 | 2.0 | 2.0 | 2.0 |
| 4-androsten-3-one-17β-carboxylic acid | — | — | — | 0.1 |

(Method of preparation)

Oxendolone or 4-androsten-3-one-17β-carboxylic acid and hardened castor oil/40 mole E0 adduct were added to 95% ethanol, and the mixture was stirred. Then, deionized water was added to the solution and mixed to obtain a transparent liquid hair grower.

| | Panel No. | Period of Non-application | Period of Application | Evaluation |
|---|---|---|---|---|
| Example 1 | 1 | 196 ± 35 | 137 ± 25 | + |
| | 2 | 352 ± 32 | 294 ± 51 | + |
| | 3 | 231 ± 25 | 176 ± 25 | + |
| | 4 | 156 ± 25 | 172 ± 40 | – |
| | 5 | 369 ± 51 | 281 ± 57 | ++ |
| | 6 | 199 ± 25 | 190 ± 21 | – |
| | 7 | 231 ± 29 | 179 ± 44 | + |
| | 8 | 156 ± 24 | 179 ± 51 | – |
| | 9 | 403 ± 52 | 351 ± 45 | + |
| | 10 | 234 ± 28 | 196 ± 31 | ± |
| Example 2 | 1 | 183 ± 45 | 141 ± 36 | + |
| | 2 | 235 ± 52 | 236 ± 48 | – |
| | 3 | 432 ± 36 | 353 ± 49 | + |
| | 4 | 295 ± 56 | 211 ± 41 | ++ |
| | 5 | 334 ± 43 | 285 ± 32 | + |
| | 6 | 342 ± 70 | 260 ± 52 | ++ |

-continued

| | Panel No. | Period of Non-application | Period of Application | Evaluation |
|---|---|---|---|---|
| | 7 | 345 ± 51 | 301 ± 42 | + |
| | 8 | 365 ± 40 | 215 ± 37 | + |
| | 9 | 412 ± 42 | 365 ± 40 | + |
| | 10 | 259 ± 25 | 201 ± 31 | + |
| Example 3 | 1 | 362 ± 75 | 261 ± 67 | ++ |
| | 2 | 234 ± 32 | 190 ± 36 | + |
| | 3 | 289 ± 51 | 212 ± 43 | ++ |
| | 4 | 361 ± 42 | 296 ± 33 | + |
| | 5 | 412 ± 54 | 365 ± 45 | + |
| | 6 | 326 ± 74 | 245 ± 60 | ++ |
| | 7 | 296 ± 46 | 241 ± 38 | + |
| | 8 | 156 ± 21 | 112 ± 25 | + |
| | 9 | 468 ± 44 | 329 ± 36 | ++ |
| | 10 | 325 ± 38 | 285 ± 31 | + |
| Comparative Example 1 | 1 | 310 ± 61 | 314 ± 56 | − |
| | 2 | 289 ± 41 | 276 ± 45 | ± |
| | 3 | 421 ± 26 | 379 ± 36 | + |
| | 4 | 189 ± 27 | 134 ± 3 | + |
| | 5 | 261 ± 48 | 273 ± 46 | − |
| | 6 | 248 ± 26 | 239 ± 29 | − |
| | 7 | 462 ± 43 | 419 ± 38 | + |
| | 8 | 326 ± 61 | 329 ± 60 | − |
| | 9 | 466 ± 39 | 412 ± 45 | + |
| | 10 | 242 ± 29 | 191 ± 31 | + |

All the results given above show that the hair grower in accordance with this invention containing oxendolone has a better hair-growing effect than the conventional hair-preparation containing 4-androsten-3-one-17β-carboxylic acid.

EXAMPLE 4

Hair-grower 2.0 g of polyoxyethylene (8 moles) oleyl alcohol ether, 0.05 g of oxendolone and 0.05 g of hinokitiol were added to 55.0 g of ethanol, perfume and dye were added in suitable amounts. Then, 42.45 g of deionized water was added to the resulting solution to obtain a hair-grower.

When this hair-grower was used actually in the same way as in Example 1, its superior hair-growing effect was ascertained.

EXAMPLE 5

Oxendolone (0.5 g), 2.0 g of polyoxyethylene (60 moles)/hardened castor oil, 10.0 g of glycerol, 10.0 g of dipropylene glycol, 5.0 g of 1,3-butylene glycol, and 5.0 g of polyethylene glycol 1500 were dissolved by heating at 60° C. (A). Cetyl isooctanoate (10.0 g), 5.0 g of squalane, 2.0 g of vaseline and 2.0 g of propyl p-oxybenzoate were dissolved by heating at 60° C. (B). 30.0 g of a 1% aqueous solution of carboxyvinyl polymer and 0.03 g of sodium hexametaphosphate were dissolved in 8.35 g of deionized water (C). A and B were mixed at 60° C. and treated in a homomixer to form a gel. Deionized water (5.0 g) was gradually added to the gel and the mixture was dispersed by a homomixer. Then, C was added and finally a solution of 0.12 g of potassium hydroxide in 5.0 g of deionized water was added. The mixture was emulsified by a homomixer to form an O/W emulsion-type hair-grower.

EXAMPLE 6

Liquid paraffin (5.0 g), 5.5 g of cetostearyl alcohol, 5.5 g of vaseline, 3.0 g of glyceryl monostearate, 3.0 g of polyoxyethylene (20 moles) 2-octyl dodecyl ether, 0.05 g of vitamin E acetate, 0.3 g of propyl p-oxybenzoate and 0.05 g of a perfume were dissolved by heating. Then, a solution of 0.5 g of oxendolone, 7.0 g of glycerol, 20.0 g of dipropylene glycol, 5.0 g of polyethylene glycol 4000, 0.005 g of sodium hexametaphosphate and 45.095 g of deionized water obtained by heating was added. The resulting mixture was emulsified by a homomixer to obtain a cream-like hair-grower.

EXAMPLE 7

The following preparations were used in the tests (1)-(22). MPB represents male pattern baldness.

| | | |
|---|---|---|
| Solution 1 | | |
| Oxendolone | 200 | mg |
| 70% ethanol | 100 | ml |
| Solution 2 | | |
| Oxendolone | 100 | mg |
| 70% ethanol | 100 | ml |
| Cream 1 | | |
| Oxendolone | 0.2 | (weight %) |
| squalane | 15 | |
| stearic acid | 3 | |
| stearyl alcohol | 3.5 | |
| vaseline | 2 | |
| stearyl monoglycelide | 2 | |
| glyceline | 5 | |
| propylene glycol | 5 | |
| potassium hydroxide | 0.2 | |
| butyl p-oxybenzoate | 0.05 | |
| distilled water | 64.05 | |
| | 100.00 | |

(1) MPB; 32-year-old male, living in Kyoto City.

Prominent hair loss started 2 years ago, and marked hair loss occurred during the summer to fall of 1981, causing recession of the hairline in the anterior portions of the calvarium. He was examined at the Department of Dermatology, Kyoto University Hospital for about 2 months and was instructed to apply about 2 ml of the solution 1 to the affected area once a day at bedtime. As a result, the soft hairs in the borders became harder, and objectively also, the hairline at the anterior portions definitely descended.

Appreciable hair loss was no longer observed. No side effect was noted, either.

(2) MPB; 24-year-old male, living in Kyoto City.

He became aware in November 1980 that hair loss was on the increase and was treated by his local home doctor and at Kyoto University Hospital without success. Then, in compliance with the instruction, he continued to rub about 3 ml of the solution 1 into the border of the hair in the anterior portion once a day from the end of December 1981. As a result, descent of the hairline by about 5 mm was noticed in about 1 month.

In addition, there was an increase of soft hairs in the anterior portions. He is under follow-up. No side effect has been observed.

(3) Alopecia areata; 24-year-old female, living in Shiga Pref.

Figure 1:
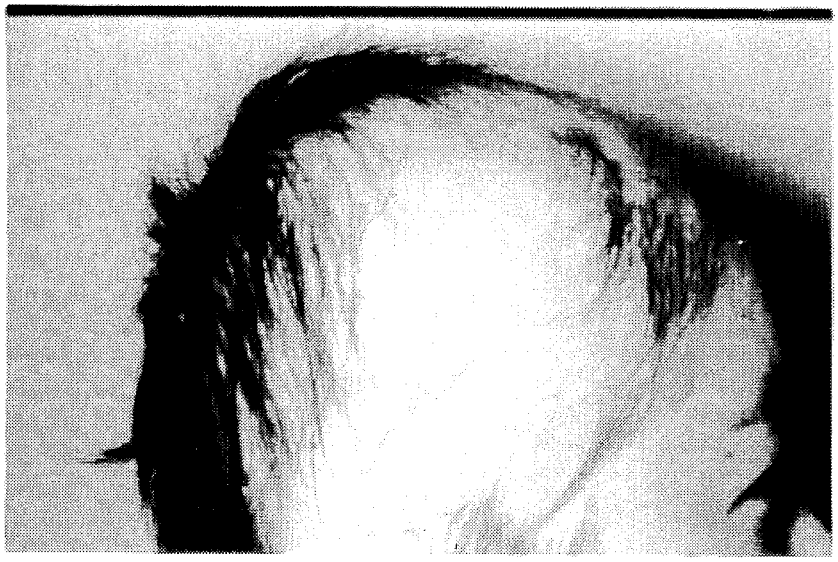
FIGS. 1–6 depict clinical studies of the instant invention.
Figure 2:
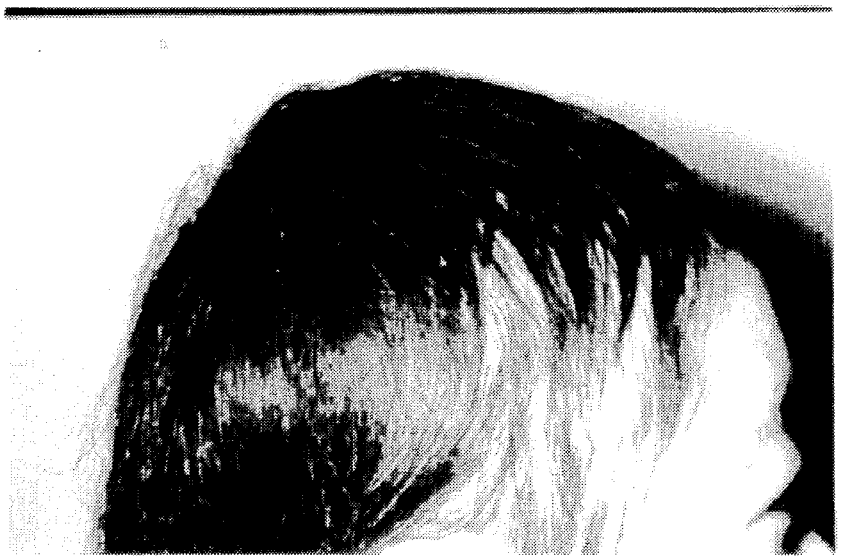

She noticed a patch of hair loss in the right lateral portion of the calvarium in August 1981. Subsequently, hair loss gradually spread over the entire scalp, and she was treated by a local home doctor. However, as hair loss steadily increased she was examined at the Department of Dermatology, Kyoto University Hospital on October 20 of the same year. The diagnosis of a malignant type of alopecia areata was made clinically and by biopsy, and she was treated for about 2 months. However, marked hair loss was persistent, advancing to the degree where almost the entire scalp was bare. Tentatively, application of about 5 ml of the solution 1 once a day was attempted, and in about 1 month almost the entire bare area showed regrowth of new soft hairs. In about one and one half months, these soft hairs turned thick and black in some portions. Hard hairs appeared over the entire scalp in about 2 months and recovered completely in about 6 months (FIGS. 1 and 2). In this case, the present solution 1 was apparently so effective that improvement was obtained in a markedly shorter period than the usual therapeutic course. No particular side effect was noted.

(4) MPB; 33-year-old male, living in Kyoto City.

Figure 3:
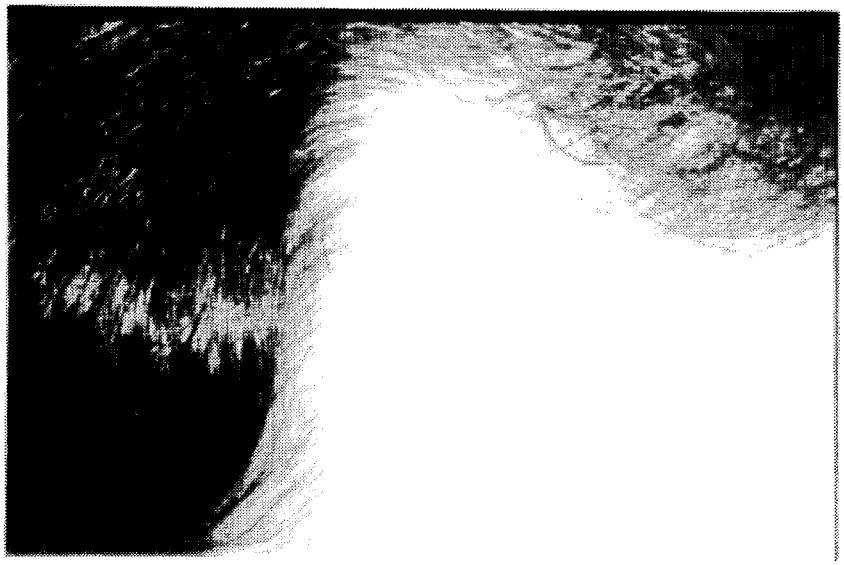
Figure 4:
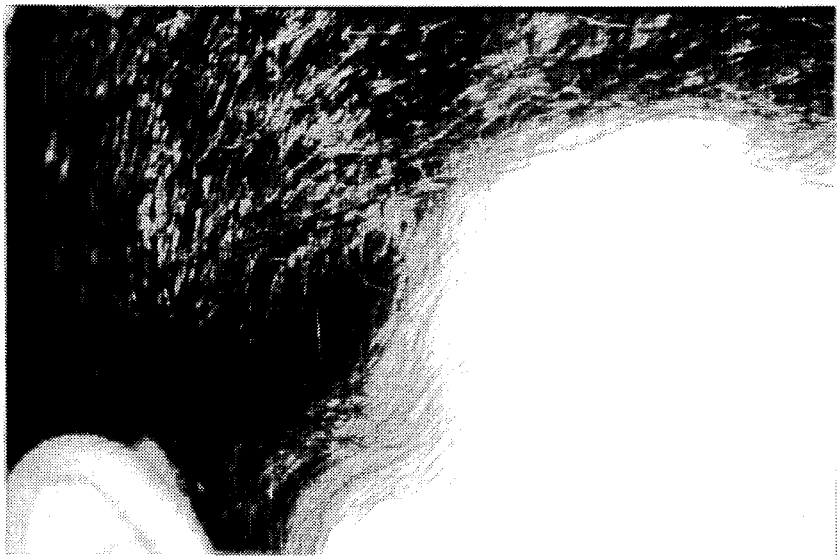

Hair loss has been increasing in the anterior to lateral portions of the calvarium from the time when he was about 20 years old. After the age of 30, hair loss seemed to increase because of stress related to his job. On Jan. 13, 1982 he was examined at the Department of Dermatology, Kawabata Hospital with chief complaint of hair loss, accompanied by an itching sensation. He was told to rub about 5 ml of the solution 1 into the entire head once a day. As a result of this therapy, decrease in hair loss and disappearance of the itching sensation were noted in about 1 month and, about 4 months later, he got well (FIGS. 3 and 4). No side effect has been noted.

(5) Alopecia areata; 29-year old female, living in Nagaokakyo City.

She had been treated by her local doctor for annular erythema of the face that used to appear around April annually. A marked hair loss occurred suddenly in the parietal portion on Dec. 17, 1981, and the entire head became almost completely bare in about a week. She was examined at the Department of Dermatology, Kyoto University Hospital on Jan. 7, 1982. No mental problems, nor abnormalities of the internal organs were observed. Because of disappearance of some hairs from the eyebrow and soft hairs from the forearm, the diagnosis of alopecia universalis was made. The solution 1 was prescribed for application of 5–7 ml over the entire head once a day. After about one and one half months with this regimen, growth of new roots of hair as black spots was noted over the entire scalp and the soft hair has observed after two months. No particular side effect has been observed.

(6) Alopecia areata; 45-year-old male, living in Shiga Prefecture.

He had had an itching sensation of the head for about 20 days. He noticed an increased hair loss 7 days previously and multiple spots of hair loss about 4 days previously. On Dec. 15, 1981, he was examined at the Department of Dermatology, Kyoto University Hospital. No mental stress, nor hematological abnormalities were observed. Clinically, multiple alopecia areata was suspected, and he was given a marketed hair grower for local application. Hair loss was still present, with formation of spots in a moth-eaten pattern. Since no appreciable change was obtained after the lapse of one and one half months, the solution 1 was prescribed for application of about 4 ml to the affected area once a day. As a result, hair loss was no longer observed 3 weeks later, and new growth of soft hairs was noted in the parietal region, followed by complete recovery after 4 months. No side effect was observed.

(7) MPB; 36-year-old female, living in Kyoto City.

Figure 5:
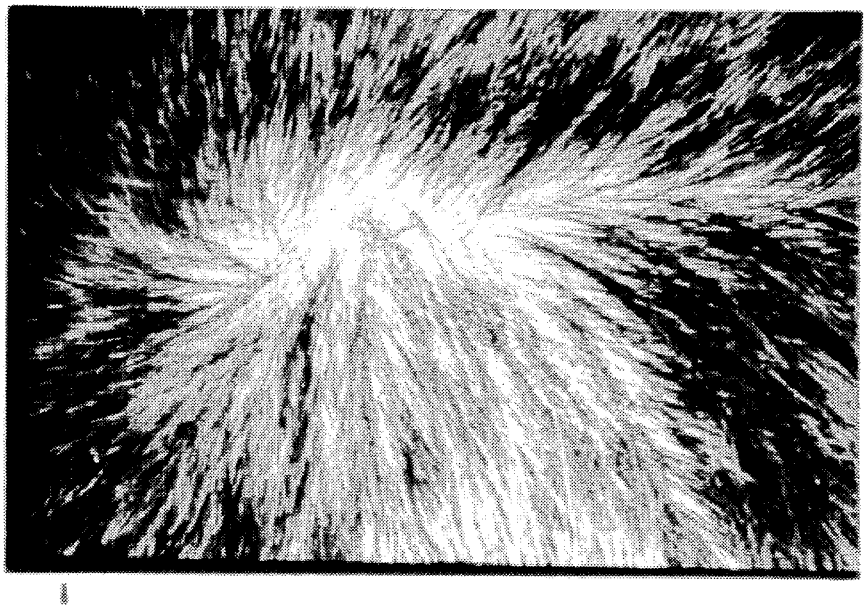
Figure 6:
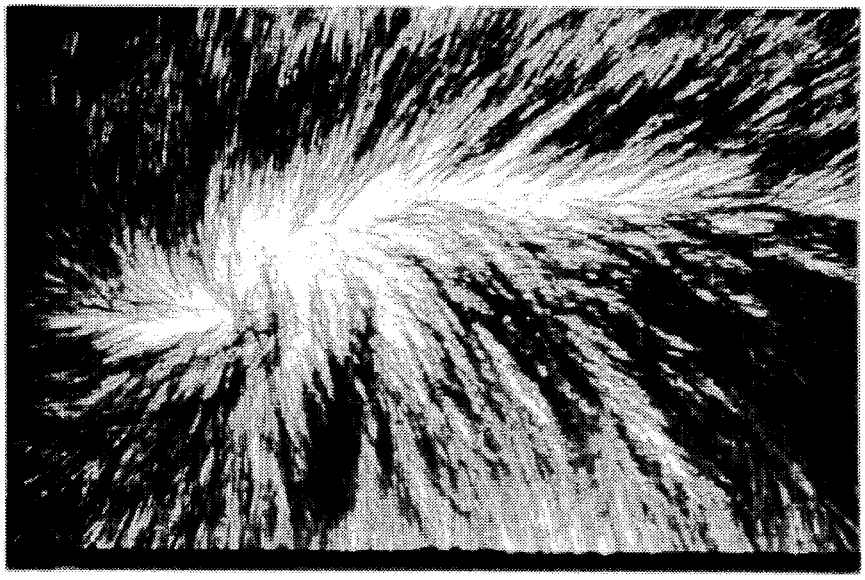

After she had a permanent wave treatment of the hair around 1960, an irritating sensation was felt in the occipital region. Then, she noticed the loss of the hair which gradually became prominent. She left the condition uncured for a while, but as the symptoms did not improve she visited the Department of Dermatology, Kyoto University Hospital on Jan. 19, 1982. The solution 1 was prescribed for application of about 5 ml over the entire head, especially at the parietal region, once a day. In consequence, hair loss was reduced to a half in one week, and there was no longer an appreciable loss of hairs 1 month later. In addition, the hair became thicker as a whole, with an increased texture improvement. Thus, a definite clinical improvement was observed (FIGS. 5 and 6). No side effect was found.

(8) MPB; 25 year-old male living in Otsu City, Shiga Prefecture.

The hairline in the anterior region started to recede at the age of 21. Hair loss seemed prominent in the fall to winter season. He was examined at the Department of Dermatology, Kyoto University Hospital on Feb. 9, 1982. After he applied about 2 ml the solution 1 to the anterior region once a day for about 1 month, growth of new soft hairs in the same region became prominent. No side effect was observed.

(9) MPB; 22-year-old male, living in Kyoto City.

In the spring of 1980, the hairline at both corners of the forehead started receding. Then, hairs over the entire anterior region began to decrease. There was a marked dandruff in the balding area at the same time. He was examined at the Department of Dermatology, Kyoto University Hospital on Sep. 3, 1981. Resorcinol and other lotions were prescribed for application, but they caused no appreciable change. From Feb. 4, 1982 he used the solution 1 by rubbing about 3 ml into the frontal to parietal region once a day. As a result, he noticed an increase of soft hairs in the same region in about 1 month. No side effect has been observed.

(10) Alopecia areata; 36-year-old female, living in Shiga Prefecture

Localized baldness, about 2 cm in diameter, was noted in the occipital region in the beginning of June, 1981. She was examined at the Department of Dermatology, Shiga College of Medical Science and treated without avail, the bald area being rather increased. Then, she visited the Department of Dermatology, Kyoto University Hospital on Feb. 4, 1982. She was instructed to rub about 0.5 ml of the solution 1 into two localized bald areas once a day. Mild growth of new soft hairs was noted in 2 weeks, and definite growth of new soft hairs was observed over the entire bald areas after another 4 weeks. Side effects have not been observed.

(11) Alopecia areata: 11year-old female, living in Kyoto City.

In 1977, she was examined and treated at the Department of Dermatology, Kyoto University Hospital for the hair loss and baldness of the parietal region which had been persisting for 2 years. Although treatment was continued, hair loss was persistent and gradually expanding. Although spontaneous growth of soft hairs was then noted during a short spell of time, hair loss began to increase again in the summer of 1981 and did not improve. With a diagnosis of alopecia areata of unknown cause, she was further treated at the Department of Neurology, Kyoto Prefectural College of Medicine. At the same time, various tests were performed there, but no abnormality was found. On Feb. 2, 1982 she was again examined at the Department of Dermatology, Kyoto University Hospital. She applied about 4 ml each of the solution 1 twice a day, in the morning and night. As a result, a mixed population of soft and hard hairs began to grow in about 1 month. No side effect has been observed.

(12) MPB; 27-year-old male, living in Tokyo.

At the age of about 22 he became aware of an increasing hair loss which used to be pronounced in the fall. He left it untreated thinking that it was hereditary since his father had also a typical senile baldness. When he became 27 years old, his hair looked so thin that the scalp in the parietal region was exposed. On Mar. 12, 1982 he was examined at dermatological section of Ijinkai Takeda Hospital through his brother's introduction. Examination revealed only thinning of the hair in the parietal region with no accompanying itching or dandruff, leading to the diagnosis of MPB. Five ml each of solution 2 was prescribed for application to the parietal region twice daily. As a result, the hair loss which used to be about 100 hairs daily decreased to about 60. On examination on Sep. 17, 1982 regrowth of numerous soft hairs was noted in the parietal region. No local or systemic side effect has been observed.

(13) Alopecia areata, 29-year-old female, living in Hikone City, Shiga Pref.

Remarkable loss of hair occurred in the parietal region from the end of January 1982. In February, the diagnosis of alopecia areata was made by a local dermatologist. Ointment and medicine were administered for about one month, but alopecia did not improve, hair loss expanding to the temporal region bilaterally. Then, hormone injection and another drug for topical use were given, but no improvment was noted. On Apr. 5, 1982 she was examined at the Dept. of Dermatology, Kyoto University Hospital. Hematological examinations were all normal and no particular mental stress was found. The only finding was a diffuse hair loss in the parietal region and the bilateral temporal regions. For comparison, solution 1 and cream 1 were applied to right and left temporal area, respectively. Two weeks later, while hair loss was persistent, regrowth of new soft hair was noted over the entire areas of hair loss. At 6 weeks, there was no longer hair loss, with regrowth of numerous soft hairs. Alopecia areata completely healed in about 3 months. No particular difference was found between solution 1 and cream 1 but, regarding applicability, the patient had a better impression with the solution.

(14). Alopecia areata, 33-year-old female, living in Otsu City, Shiga Pref.

Hair loss round in shape, appeared in the parietal portion in December 1980, and she was treated with ointment as well as medicine at Japan Red Cross Hospital at Otsu. Since, in spite of the treatment, hair loss continued, topical and oral steroids were prescribed at the Dept. of Dermatology, Kyoto University Hospital in January 1981. She followed the instructions for one month, but hair loss was still persistent. The treatment was switched to an oral steroid alone. Then, hair loss decreased in 2–3 months, and the oral steroid was suspended. As a result, hair loss increased again, and in spite of subsequent various ways of treatment, no improving tendency was noted. In January 1982, she started embrocating cream 1, and a marked regrowth of soft and hard hairs was observed in about 1½ months.

(15) MPB; 32-year-old male, living in Kyoto City.

His forehead was rather wide from the birth, and hair loss increased 2 years ago, In addition, recession of the hairline in the frontal region was observed. His job was a source of much stress, and hair loss was observed all the year around, having the tendency of increase when there was an increase in dandruff. He embrocated 2 g each of cream 1 prescribed at Kyoto Univ. Hospital into the borders of hairs in the frontal portion once a day from June 1982. In about one week, decreases in dandruff and in hair loss were noted. At one month, regrowth of a few soft hairs was found in both corners of the forehead.

(16) MPB; 52-year-old male, living in Kyoto City.

The hair in the parietal portion was thin because of the scar of a trauma he received to the head in his childhood. For this reason he used to wear a wig. The hair from the frontal to parietal portions became thinner as a whole about 5 years ago, and he was examined at the Dept. of Dermatology, Kyoto University Hospital on Jul. 22, 1982. He received 2 g each of cream 1 and embrocated it into the affected area 1–2 times a day. About one month later, a decrease in hair loss and regrowth of soft hairs were observed. When he visited the hospital about 4 months later his hair appeared thicker, and he told us that hardly any hairs adhered to his wig any more. He is under follow-up, and no side effect has been seen.

(17) MPB; 60 years old, male, living in Kyoto City.

The subject noticed an increased loss of hair around 40 years old. He has tried various tonics sold on the market or treated by a physician nearby. But no remarkable effect was observed. During this time, the loss of hair extended from the forehead portion to the vertex portion, and he almost gave up hope of recovery. When solution 1 was applied to him in an amount of 5 ml once a day from June 1982, soft hairs. newly grew in the forehead portion in about one month, and in two months, soft hairs increased at the vertex portion. The subject is now placed under observation for progress. No side-effect has been observed.

(18) MPB; 48 years old, male, living in Kyoto City.

Loss of hair has rapidly increased since 13 years ago, and in the past 4 or 5 years, the hairs at the forehead portion to the vertex portion became sparce. Almost all hairs have been replaced by soft hairs. For this reason, the subject once used a "wig" 7 or 8 years ago. He tried commercially available drugs, but obtained no effect. Thus, he visited the Department of Dermatology, Kyoto University Hospital for treatment. So solution 1 was dispensed in an amount of 5 ml once a day. In about one month, soft hairs newly grew in the forehead portion, and after about further three months, soft hairs grew in the forehead portion to a visible extent.

(19) MPB; 32 years old, male, living in Kyoto-City.

The subject noticed increasing itching and seborrhea at the head, but left it without treatment. Soon, reddening appeared in the forehead portion, and loss of hair increased. Since the hairline at the forehead rose, he hurriedly began to use 5 ml each of solution 1 once a day in December 1981. In about one month, reddening, itching and loss of hair decreased, and in about 3 months, hard hairs were seen to grow. He has continued to use solution 1. No side-effect has been observed. This is a case of the inventor himself.

(20) MPB; 52 years old, female, living in Kyoto City.

After death of a relative about 12 years ago, diffuse loss of hair occurred. She then visited the Department of Dermatology, Kyoto University Hospital. She used the dispensed drug but no improvement was seen. Thereafter, she gave up hope for recovery about loss of hair. When she again visited the Department of Dermatology, Kyoto University Hospital for treatment, 5 ml of solution 1 was dispensed. In about one week, itching at the head ceased, but no change was seen in the amount of hairs lost. In about 2 weeks, the amount of hair lost was reduced to half, and soft hairs were seen to grow newly. About one and one half months later, the amount of hair in the entire head increased, and the amount of hair lost was about half of that before. When she visited the hospital about 4 months later, the hair at the forehead evidently became thicker.

(21) MPB; 37 years old, male, living in Kyoto City.

About one year and two months ago, the subject noticed a large loss of hair accompanied by itching and a large amount of dandruff. There was no mental stress. For this reason, he visited the Department of Dermatology, Kyoto University Hospital. The present solution 1 was dispensed. When he visited the hospital about one month later, itching and dandruff decreased, and the amount of hairs lost somewhat decreased.

(22) MPB; 59 years old, male, living in Ikoma City, Nara Prefecture.

About 5 years ago, dandruff at the forehead portion to the vertex portion increased, and at the same time, loss of hair began to increase. There was no particular mental stress. For this reason, the subject began to use 5 ml each of solution 1 once a day in April 1982. In about one month, dandruff and loss of hair were seen to decrease, and at the same time soft hairs newly grew. He continued to use solution 1. Now, the scarce portion of the hair at the vertex became visibly black. There was no particular side-effect.

(23) Summary of the Cases

① MPB

Of the total 43 cases, 35(81%) were men and 8(19%) women. The following tables show the age distribution and duration of illness.

Age Distribution:

| Age | Number of Persons | % |
|---|---|---|
| 16–20 | 4 | 8.9 |
| 21–25 | 12 | 26.7 |
| 26–30 | 6 | 13.3 |
| 31–35 | 9 | 20.0 |
| 36–40 | 4 | 8.9 |
| 41–45 | 2 | 4.4 |
| 46–50 | 1 | 2.2 |
| 51–55 | 2 | 4.4 |
| 56–60 | 3 | 6.7 |

Duration of illness:

| Time (year) | Number of Persons | % |
|---|---|---|
| less than 1 | 7 | 15.6 |
| 1–5 | 23 | 51.1 |
| 6–10 | 6 | 13.3 |
| 11–15 | 6 | 13.3 |
| 16–20 | 2 | 4.4 |
| more than 20 | 1 | 2.2 |

Of these cases, a definite effect observed in 32 cases which are detailed below.

The duration until manifestation of the effect:

| Time | Number of Persons | % |
|---|---|---|
| 1–2 weeks | 3 | 6.7 |
| 3–4 weeks | 3 | 6.7 |
| 1–2 months | 14 | 31.1 |
| 2–3 months | 4 | 8.9 |
| 3–4 months | 6 | 13.3 |
| more than 4 months | 2 | 4.4 |

Changes in individual symptoms:

| Symptoms | Number of Persons | % |
|---|---|---|
| 1. Decrease in hair loss | 25 | 75.8 |
| 2. Regrowth of downy hair | 16 | 48.5 |
| 3. Regrowth of thick hair | 7 | 21.2 |
| 4. Decrease in itching sensation | 6 | 18.2 |
| 5. Decrease in dandruff | 3 | 9.1 |
| 6. Decrease in the sebum | 1 | 3.0 |

② Alopecia areata

This condition was observed in 41 cases consisting of 16 males (39%) and 25 females (61%). The age distribution and duration of illness are shown below.

Age Distribution:

| Age | Number of Persons | % |
|---|---|---|
| 1–10 | 2 | 4.9 |
| 11–20 | 10 | 24.4 |
| 21–30 | 7 | 17.1 |
| 31–40 | 11 | 26.8 |
| 41–50 | 6 | 14.6 |
| 51–60 | 5 | 12.2 |

Duration of illness:

| Time | Number of Persons | % |
|---|---|---|
| 4–6 months | 10 | 24.4 |
| 7–12 months | 9 | 22.0 |
| 1–5 years | 16 | 39.0 |
| 6–10 years | 4 | 9.8 |
| 11–20 years | 2 | 4.9 |

Of this population, the treatment was effective in 35 (85%). The following tables show the duration until manifestation of the effect and changes of individual symptoms.

Duration until manifestation of the effect:

| Time | Number of Persons | % |
|---|---|---|
| less than one month | 19 | 54.3 |
| 2–3 months | 15 | 42.9 |
| 4–5 months | 1 | 2.9 |

Changes of individual symptoms:

| Symptoms | Number of Persons | % |
|---|---|---|
| Regrowth of soft hair | 33 | 94.3 |
| Regrowth of thick hair | 10 | 28.6 |
| Decrease in hair loss | 6 | 17.1 |
| Decrease in itching sensation | 2 | 5.7 |
| Increased perspiration | 1 | 2.9 |

Having thus described the invention, what is claimed is:

1. A method for reducing hair loss from the human scalp in male pattern baldness, which comprises topically applying a composition comprising up to 2% of oxendolone in combination with a topically applicable vehicle or carrier thereof to the human scalp.

2. A composition for topical application to reduce hair loss from the human scalp in male pattern baldness, comprising up to 2% of oxendolone in combination with a topically applicable vehicle or carrier thereof.

3. A composition as claimed in claim 2, wherein the topically applicable vehicle or carrier is an aqueous solution containing at least 30 weight percent of ethanol.

4. A composition as claimed in claim 2, wherein the content of oxendolone is 0.001–2% relative to the total composition.

* * * * *